(12) United States Patent
Adams et al.

(10) Patent No.: US 6,306,883 B1
(45) Date of Patent: Oct. 23, 2001

(54) COMPOUNDS

(75) Inventors: Jerry Leroy Adams, Wayne; Timothy Francis Gallagher, Harleysville; Ravi Shanker Garigipati, Wayne; Susan Mary Thompson, Phoenixville, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/456,019

(22) Filed: Dec. 3, 1999

Related U.S. Application Data

(60) Division of application No. 08/454,170, filed as application No. PCT/US95/06297 on Jun. 16, 1995, now Pat. No. 5,998,425, which is a continuation-in-part of application No. 08/242,906, filed on May 16, 1994, now Pat. No. 5,559,137.

(51) Int. Cl.$^7$ ................. C07D 401/04; A61K 31/444
(52) U.S. Cl. ............................... 514/333; 546/256
(58) Field of Search ................ 546/256; 514/333

(56) References Cited

PUBLICATIONS

CA 130:25069, Anantanarayan et a. 1988.*
CA 82: 140006, Moerck et al. 1975.*

* cited by examiner

*Primary Examiner*—Jane Fan
(74) *Attorney, Agent, or Firm*—Dara L. Dinner; Stephen Venetianer; Charles M. Kinzig

(57) ABSTRACT

This invention relates to the novel pyrazole compounds of Formula (I), and pharmaceutical compositions comprising a compound of formula (I) and a pharmaceutically acceptable diluent or carrier.

This invention also relates to a method of inhibiting cytokines by a compound of formula (I) and the treatment of cytokines mediated diseases, in mammals, by administration of said compound.

10 Claims, No Drawings

COMPOUNDS

This application is a divisional of U.S. Ser. No. 08/454,170, filed Nov. 15, 1996 (now U.S. Pat. No. 5,998,425) and which application is the § 371 national stage entry of PCT/US95/06297, filed Jun. 16, 1995, which is a continuation in part application of U.S. Ser. No. 08/242,906, filed May 16, 1994, now U.S. Pat. No. 5,559,137).

FIELD OF THE INVENTION

This invention relates to a novel group of pyrazole compounds, processes for the preparation thereof, the use thereof in treating cytokine mediated diseases and pharmaceutical compositions for use in such therapy.

BACKGROUND OF THE INVENTION

Interltelin-1 (IL-1) and Tumor Necrosis Factor (TNF) ame biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neumphil chemotaxis, induction of acute phase proteins and the supp on of plasma iron levels.

There are many disease states in which excessive or unregulated IL-1 production is implicated in exacerbating and/or causing the disease. These include rheumatoid arthitis, osteoartntis, cndotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthitis, rubella arthitis, and acute synovitis. Recent evidence also links IL-1 activity to diabetes and pancreatic βcells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty.arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulccative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monoldne activity such as by inhibition of monoldne production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782–784 (1990)], therefore, inhibition of monoldne production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrphils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophils into the inflammatory site) would benefit by compounds which art suppressive of IL-8 pduction.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are capable of inhibiting cytokines, such as IL-1, IL-6, IL-8 and TNF.

SUMMARY OF THE INVENTION

This invention elates to the novel compounds of Formula (I) and pharmaceutical compositions comprising a compound of Formula (I) and a pharmaceutically acceptable diluent or carrier.

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

DETAILED DESCRIPTION OF THE INVENTION

The novel compounds of this invention are represented by the structure having the formula (I):

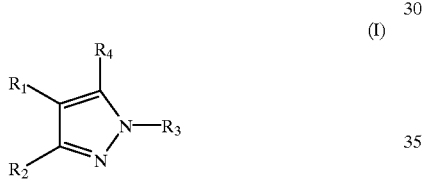

(I)

wherein one of $R_1$ and $R_2$ is selected from is 4-pyridyl, 4-pyrimidinyl, 4quinolyl, 4-isoquinolinyl 4-quinazolinyl, which is optionally substituted with one or two substituents each of which is independently selected from $C_{1-4}$ alkyl, halo, $C_{1-4}$ alkoxy, $C_{1-4}$ alyklthio, $CH_2OR_8$, $NH_2$, mono- or di-$C_{1-6}$-alkylamino or N-heterocyclyl ring which ring has from 5 to 7 members and optionally contains an additional heteratom selected from oxygen, sulfur or $NR_{22}$; and the other of $R_1$ and $R_2$ is selected from an optionally substituted aryl or optionally substituted hetcolyl group, provided that both $R_1$ and $R_2$ are not the same heteroaryl group; wherein when one $R_1$ and $R_2$ is an optionally substituted aryl ring, the ring is substituted by one or two substituents, each of which is independently selected, and which, for a 4-phenyl, 4-naphth-1-yl or 5-naphth-2-yl substituent, is halo, nitro, cyano, —$C(Z)NR_7R_{17}$, —$C(Z)OR_{23}$, —$(CR_{10}R_{20})_nCOR_{36}$, —$SR_5$, —$S(O)R_5$, —$OR_{36}$, halo-substituted $C_{1-4}$ alkyl, $C_{1-4}$ alkyl, —$ZC(Z)R_{36}$, —$NR_{10}C(Z)R_{23}$, or —$(CR_{10}R_{20})_n$ $NR_{10}R_{20}$ and which, for other positions of substitution, is halo, —$(CR_{10}R_{20})_n$nitro, —$(CR_{10}R_{20})_n$cyano, —$(CR_{10}R_{20})_nC(Z)NR_{16}R_{26}$, —$(CR_{10}R_{20})_nC(Z)OR_{18}$, —$(CR_{10}R_{20})_nCOR_{25}$, —$(CR_{10}R_{20})_n$—$S(O)_mR_8$, —$(CR_{10}R_{20})_nOH$, —$(CR_{10}R_{20})_nOR_{25}$, halo-Substituted-$C_{1-4}$ alykl, —$C_{1-4}$ alkyl, —$(CR_{10}R_{20})_nNR_{10}C(Z)R_{25}$, —$(CR_{10}R_{20})_nNHS(O)_mR_6$, —$(CR_{10}R_{20})_nNHS(O)_mNR_7R_{17}$, —$(CR_{10}R_{20})_nNR_6S(O)_mR_6$, —$(CR_{10}R_{20})_nNR_6S(O)_m'NR_7R_{17}$; —$(CR_{10}R_{20})_nZC(Z)R_{18}$ or —$(CR_{10}R_{20})_nNR_7R_{17}$; and when one of $R_1$ and $R_2$ is an optionally substituted heteroaryl group, the substituent groups include one or two substituents each of which is independently selected from $C_{1-4}$ alkyl halo, $C_{1-4}$ alkoxy, $C_{1-4}$ alkylthio, $NR_{10}R_{20}$, or an N-hetercyclyl ring which ring has from 5 to 7 members and optionally contains an additional heteroatom selected from oxygen, sulfur or $NR_{12}$;

n is 0 or an integer of 1 or 2;

n' is 0 or an integer having a value of 1 to 10;

n" is an integer having a value of 1 to 10;

m is 0 or an integer of 1 or 2;

m' is an integer of 1 or 2;

m" is an integer having a value of 1 to 10;

$R_3$ is $Q-(Y_1)_t$;

Q is an aryl or heteroaryl group;

t is an integer having a value of 1 to 3;

$R_4$ is hydrogen, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl-$C_{1-10}$ alkyl, aryl, aryl$C_{1-10}$ alkyl, heteroaryl, heteroaryl-$C_{1-10}$-alkyl, heterocyclyl, heterocyclyl$C_{1-10}$ alkyl, —$(CR_{10}R_{20})_n$'$OR_{12}$, $(CR_{10}R_{20})_nOR_{13}$, $(CR_{10}R_{20})_nS(O)_mR_{18}$, $(CR_{10}R_{20})_nNHS(O)_2R_{18}$, $(CR_{10}R_{20})_nNR_{16}R_{26}$, $(CR_{10}R_{20})_nNO_2$, $(CR_{10}R_{20})_nCN$, $(CR_{10}R_{20})_n'SO_2R_{18}$, $(CR_{10}R_{20})_nS(O)_m'NR_{16}R_{26}$, $(CR_{10}R_{20})_nC(Z)R_{13}$, $(CR_{10}R_{20})_nOC(Z)R_{13}$, $(CR_{10}R_{20})_nC(Z)OR_{13}$, $(CR_{10}R_{20})_nC(Z)NR_{16}R_{26}$, $(CR_{10}R_{20})_nC(Z)NR_{13}OR_9$, $(CR_{10}R_{20})_nNR_{10}C(Z)R_{11}$, $(CR_{10}R_{20})_nNR_{10}C(Z)NR_{16}R_{26}$, $(CR_{10}R_{20})_nN(OR_6)C(Z)NR_{16}R_{26}$, $(CR_{10}R_{20})_nN(OR_6)C(Z)R_{13}$, $(CR_{10}R_{20})_nC(=NOR_6)R_{13}$, $(CR_{10}R_{20})_nNR_{10}C(=NR_{19})NR_{16}R_{26}$, $(CR_{10}R_{20})_nOC(Z)NR_{16}R_{26}$, $(CR_{10}R_{20})_nNR_{10}C(Z)NR_{16}R_{26}$, $(CR_{10}R_{20})_nNR_{10}C(Z)OR_{10}$, 5-($R_{18}$)-1,2,4-oxadizaol-3-yl or $R_{12}$)-5-($R_{18}R_{19}$)-4,5-dihydzo-1,2,4-oxadiazol-3-yl; wherein the aryl, arylyl, heteroaryl, heteroaryl alkyl, cyclcoalkyL cycloalkyl alkyl heterocyclic and heterocyclic alkyl groups may be optionally substitd;

$R_6$ is $C_{1-10}$ alkyl, $C_{3-7}$ cycloalkyl, aryl, aryl$C_{1-10}$alkyl, heterocyclyl, heterocyclyl $C_{1-10}$alkyl, heterocyclyl-$C_{1-10}$alkyl, heteroaryl or hetcroaryl$C_{1-10}$alkyl;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —$SOH$;

$R_{16}$ and $R_{26}$ are independently hydrogen, or $C_{1-4}$ alkyl or $R_{16}$ and $R_{26}$ together with the nitrogen to which they are attached form a heterocyclic or heteroaryl ring of 5–7 members optionally containing an additional heteroatom selected from oxygen, sulfur or $NR_{22}$;

$Y_1$ is independently selected from hydrogen, $C_{1-5}$ alkyl, halo-substituted $C_{1-5}$ alkyl, halogen, or —$(CR_{10}R_{20})_nY_2$;

$Y_2$ is hydrogen, halogen, —$OR_8$, —$NO_2$, —$S(O)_mR_{11}$, —$SR_8$, —$S(O)_m'OR_8$, —$S(O)_mNR_8R_9$, —$NR_8R_9$, —$O(CR_{10}R_{20})_n'NR_8R_9$, —$C(O)R_8$, —$CO_2R_8$, —$CO_2(CR_{10}R_{20})_m$"$CONR_8R_9$, —$ZC(O)R_8$, —$CN$, —$C(Z)NR_8R_9$, —$NR_{10}C(Z)R_8$, —$C(Z)NR_8OR_9$, —$NR_{10}C(Z)NR_8R_9$, —$NR_{10}S(O)_m'R_{11}$, —$N(OR_{21})C(Z)NR_8R_9$, —$N(OR_{21})C(Z)R_8$, —$C(=NOR_{21})R_8$, —$NR_{10}C(=NR_{15})SR_{11}$, —$NR_{10}C(=NR_{15})NR_8R_9$, —$NR_{10}C(=CR_{14}R_{24})SR_{11}$, —$NR_{10}C(=CR_{14}R_{24})NR_8R_9$, —NR$_{10}$C(O)C(O)NR$_8$R$_9$, —NR$_{10}$C(O)C(O)OR$_{10}$, —C(=NR$_{13}$)NR$_8$R$_9$, —C(=NOR$_{13}$)NR$_8$R$_9$, —C(=NR$_{13}$)ZR$_{11}$, —OC(Z)NR$_8$R$_9$, —NR$_{10}$S(O)$_m$CF$_3$, —NR$_{10}$C(Z)OR$_{10}$, 5-(R$_{18}$)-1,2,4-oxadizaol-3-yl or 4-(R$_{12}$)-5-(R$_{18}$R$_{19}$)-4,5-dihydro-1,2,4-oxadiazol-3-yl;

R$_7$ and R$_{17}$ is each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or NR$_{22}$;

R$_8$ is hydrogen, C$_{1-10}$ alkyl, C$_{3-7}$ cycloalkyl, heterocyclyl, heterocyclylC$_{1-10}$alkyl, aryl, arylC$_{1-10}$alkyl, heteroaryl or heteroarylC$_{1-10}$alkyl;

R$_9$ is hydrogen, C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylalkyl, heteroaryl or heteroarylalkyl or R$_8$ and R$_9$ may together with the nitrogen to which they are attached form a heterocyclic or heteroaryl ring of 5 to 7 members which ring optionally contains an additional heteroatom selected from oxygen, sulfur or NR$_{12}$;

R$_{10}$ and R$_{20}$ is each independently selected from hydrogen or C$_{1-4}$ alykl;

R$_{11}$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, heterocyclic, heterocyclic C$_{1-10}$alkyl, aryl, aryl C$_{1-10}$alkyl, heteroaryl or heteroaryl C$_{1-10}$alkyl;

R$_{12}$ is hydrogen, —C(Z)R$_{13}$, optionally substituted C$_{1-4}$ alkyl, optionally substituted aryl, optionally substituted aryl-C$_{1-4}$ alkyl, or S(O)$_2$R$_{18}$;

R$_{13}$ is hydrogen, C$_{1-10}$ alkyl, C$_{3-7}$ cycloalkyl, heterocyclyl, heterocyclylC$_{1-10}$ alkyl aryl, arylC$_{1-10}$alkyl, heteroaryl or heteroarylC$_{1-10}$alkyl;

R$_{14}$ and R$_{24}$ is each independently selected from hydrogen, alkyl, nitro or cyano;

R$_{15}$ is hydrogen, cyano, C$_{1-4}$ alkyl, C$_{3-7}$ cycloalkyl or aryl;

R$_{16}$ and R$_{26}$ is each independently selected from hydrogen or optionally substituted C$_{1-4}$ alkyl optionally substituted aryl or optionally substituted aryl-C$_{1-4}$ alkyl or together with the nitrogen which they are attached form a heterocyclic ring of 5 to 7 members which ring optionally contains an additional heteroatom selected from oxygen, sulfur or NR$_{12}$;

R$_{18}$ is C$_{1-10}$ alkyl, C$_{3-7}$ cycloalkyl, aryl, arylC$_{1-10}$alkyl, heterocyclyl, heterocyclyl-C$_{1-10}$alkyl, heteroaryl or hetroarylC$_{1-10}$alkyl;

R$_{19}$ is hydrogen, cyano, C$_{1-4}$ alkyl, C$_{3-7}$ cycloalkyl or aryl;

R$_{21}$ is hydrogen, a pharmaceutically acceptable cation, C$_{1-10}$ alkyl, C$_{3-7}$ cycloalkyl, aryl, arylC$_{1-4}$ alkyl, heteroaryl, hetearylalkyl, heterocyclyl, aroyl, or C$_{1-10}$ alkanoyl;

R$_{22}$ is R$_{10}$ or C(Z)-C$_{1-4}$ alkyl;

R$_{23}$ is C$_{1-4}$ alkyl, halo-substituted-C$_{1-4}$ alkyl, or C$_{3-7}$ cycloalkyl;

R$_{25}$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, heterocyclyl, hemrocyclylC$_{1-10}$ alkyl, CR$_{10}$R$_{20}$)$_n$OR$_8$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_7$R$_{17}$; wherein the aryl, arylalkyl, heteroaryl, heteroaryl alkyl may be optionally substituted;

R$_{36}$ is hydrogen or R$_{23}$;

or a pharmaceutically acceptable salt thereof.

Suitable hetemaryl moieties for R$_1$ and R$_2$ are 4-pyridyl, 4-pyrimidinyl, 4-quinolyl, or 6-isoquinolinyl, all of which may be optionally substituted. Preferably the heteroaryl group is a 4-pyndyl, 4-pyrimidinyl or 4-quinolyl. More preferred is an optionally substituted 4-pyrimidinyl or optionally substituted 4-pyridyl moiety, and most preferred is an optionally substituted 4-pyrimidinyl ring.

Suitable substituent groups for the heteroaryl moieties, R$_1$ and R$_2$, include one or two substituents each of which are independently selected from C$_{1-4}$ alkyl, halo, hydroxy, C$_{1-4}$ alloxy, C$_{1-4}$ alkylthio, C$_{1-4}$ alkylsulfinyl, CH$_2$OR$_8$, amino, mono- or di-C$_{1-6}$ alkyl substituted amino, or an N-heterocyclyl ring which ring has from 5 to 7 members and optionally contains an additional heteroatom selected from oxygen, sulfur or NR$_{22}$.

Preferred substituents for the heteroaryl moieties R$_1$ is C$_{1-4}$ alkyl, amino, and mono-C$_{1-6}$alkyl substituted amino. Preferably the C$_{1-4}$ alkyl is methyl, and for the mono-C$_{1-6}$alkyl substituted amino the alkyl it is of 1-4 carbons in length or shorter, such as 1 to 2 carbons, preferably methyl. A preferred ring placement of the R$_1$ substituent on the 4-pyridyl derivative is the 2-position, such as 2-methyl-4-pyridyl. A preferred ring placement on the 4-pyrimidinyl ring is also at the 2-position, such as in 2-methyl-pyrinmidinyl, 2-amino pyrimidinyl or 2-methylaminopyrimidinyl.

For the purposes herein the "core" 4-pyrimidinyl moiety for R$_1$ or R$_2$ is referred

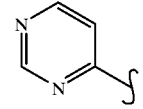

Suitable aryl groups for the other of R$_1$ or R$_2$ include optionally substituted phenyl, naphth-1-yl or naphth-2-yl. The aryl ring may be optionally substituted by one or two substituents, each of which is independently selected, and which, for a 4-phenyl, 4-naphth-1-yl or 5-naphth-2-yl substituent, is halo, nitro, cyano, —C(Z)NR$_7$R$_{17}$, —C(Z)OR$_{23}$, —(CR$_{10}$R$_{20}$)$_n$COR$_{36}$, —SR$_5$, —S(O)R$_5$, —OR$_{36}$, halo-substituted C$_{1-4}$ alkyl, C$_{1-4}$ alkyl, —ZC(Z)R$_{36}$, —NR$_{10}$C(Z)R$_{23}$, or —(CR$_{10}$R$_{20}$)$_n$NR$_{10}$R$_{20}$ and which, for other positions of substitution, is halo, nitro, cyano, —C(Z)NR$_{16}$R$_{26}$, C(Z)OR$_{18}$, —(CR$_{10}$R$_{20}$)$_n$COR$_{25}$, —S(O)$_m$R$_8$, OH, —OR$_{25}$, halo-substituted-C$_{1-4}$ alkyl, -C$_{1-4}$ alkyl, —(CR$_{10}$R$_{20}$)$_n$NR$_{10}$C(Z)R$_{25}$, —NHS(O)$_m$R$_6$, —NHS(O)$_m$NR$_7$R$_{17}$, —NR$_6$S(O)$_m$R$_6$, —NR$_6$S(O)$_m$'NR$_7$R$_{17}$ wherein m' is 1 or 2, —ZC(Z)R$_{18}$ or —(CR$_{10}$R$_{20}$)$_n$NR$_7$R$_{17}$. Preferably the aryl ring is a phenyl which is optionally substituted.

Preferred substitutions for the R$_1$ or R$_2$ group when it is a 4-phenyl, 4naphth-1-yl or 5-naphth-2-yl moiety are one or two substituents each independently selected from halogen, —SR$_5$, —SOR$_5$, —OR$_{36}$, or —(CR$_{10}$R$_{20}$)$_n$NR$_{10}$R$_{20}$, and for other positions of substitution on these rings preferred substitution is halogen, —S(O)$_m$R$_{25}$, —OR$_{25}$, —(CR$_{10}$R$_{20}$)$_n$NR$_7$R$_{17}$, —(CR$_{10}$R$_{20}$)$_n$NR$_{10}$C(Z)R$_{25}$ and —NR$_6$S(O)$_m$'R$_6$. More preferred substituents for the 4-position in phenyl and naphth-1-yl and on the 5-position in naphth-2-yl include halogen, especially fluoro and chloro, more especially fluoro, and —SR$_5$ and —S(O)R$_5$ wherein R$_5$ is preferably a C$_{1-2}$ alkyl, more preferably methyl; of which fluoro is especially preferred.

Preferred substituents for the 3-position in phenyl and naphth-1-yl include: halogen, especially chloro; $R_{25}$, especially $C_{1-4}$ alkoxy, amino; —$NR_{10}C(Z)R_{25}$, especially —$NHCO(C_{1-10}alkyl)$; and —$NR_{10}S(O)_m'R_6$, especially —$NHSO_2(C_{1-10}alkyl)$. Preferably, the aryl group is an unsubstituted or substituted phenyl moiety. More preferably, it is phenyl or phenyl substituted at the 4-position with fluoro and/or substituted at the 3-position with fluoro, chloro, $C_{1-4}$ alkoxy, methanesulfonamido or acetamido.

Suitably, $R_3$ is Q-$(Y_1)_t$ wherein Q is an aryl or heteroaryl group; and t is an integer having a value of 1 to 3. Suitably $Y_1$ is independently selected from hydrogen, $C_{1-5}$ alkyl, halo-substituted $C_{1-5}$ alkyl, halogen, or —$(CR_{10}R_{20})_nY_2$.

Suitably $Y_2$ is hydrogen, halogen, —$OR_8$, —$NO_2$, —$S(O)_m'R_{11}$, —$SR_8$, —$S(O)_m'OR_8$, —$S(O)_mNR_8R_9$, —$NR_8R_9$, —$O(CR_{10}R_{20})_nNR_8R_9$, —$C(O)R_8$, —$CO_2R_8$, —$CO_2(CR_{10}R_{20})_m''CONR_8R_9$, —$ZC(O)R_8$, —$CN$, —$C(Z)NR_8R_9$, —$NR_{10}C(Z)R_8$, —$C(Z)NR_8OR_9$, —$NR_{10}C(Z)NR_8R_9$, —$NR_{10}S(O)_m'R_{11}$, —$N(OR_{21})C(Z)NR_8R_9$, —$N(OR_{21})C(Z)R_8$, —$C(=NOR_{21})R_8$, —$NR_{10}C(=NR_{15})SR_{11}$, —$NR_{10}C(=NR_{15})NR_8R_9$, —$NR_{10}C(=CR_{14}R_{24})SR_{11}$, —$NR_{10}C(=CR_{14}R_{24})NR_8R_9$, —$NR_{10}C(O)C(O)NR_8R_9$, —$NR_{10}C(O)C(O)OR_{10}$, —$C(=NR_{13})NR_8R_9$, —$C(=NOR_{13})NR_8R_9$, —$C(=NR_{13})ZR_{11}$, —$OC(Z)NR_8R_9$, —$NR_{10}S(O)_mCF_3$, —$NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl.

Preferably Q is phenyl which is optionally substituted. Preferable substituents include —$(CR_{10}R_{20})_nY_2$ with $Y_2$ as —$S(O)_m'R_{11}$, —$SR_8$, halogen or —$C_2R_8$; n is 0 or 1.

Preferably t is 1 or 2. More preferably, when $R_3$ is monosubstituted phenyl (t=1), the substituent is located at the 4-position.

Suitably $R_4$ is hydrogen, $C_{1-10}$alkyl, halo-substituted $C_{1-10}$alkyl, $C_{2-10}$ alkenyl, $C_{2-10}$ alkynyl, $C_{3-7}$ cycloalkyl $C_{3-7}$cycloalkyl$C_{1-10}$alkyl, $C_{5-7}$ cycloalkenyl, $C_{5-7}$cycloakenyl-$C_{1-10}$ alkyl, aryl, aryl$C_{1-10}$alkyl, heteroaryl, heteroaryl-$C_{1-10}$-alkyl, heterocyclyl, heterocyclyl$C_{1-10}$ alkyl, —$(CR_{10}R_{20})_n'OR_{12}$, $(CR_{10}R_{20})_nOR_{13}$, $(CR_{10}R_{20})_nS(O)_mR_{18}$, $(CR_{10}R_{20})_nNHS(O)_2R_{18}$, $(CR_{10}R_{20})_nNR_{16}R_{26}$, $(CR_{10}R_{20})_nNO_2$, $(CR_{10}R_{20})_nCN$, $(CR_{10}R_{20})_n'SO_2R_{18}$, $(CR_{10}R_{20})_nS(O)_m'NR_{16}R_{26}$, $(CR_{10}R_{20})_nC(Z)R_{13}$, $(CR_{10}R_{20})_nOC(Z)R_{13}$, $(CR_{10}R_{20})_nC(Z)OR_{13}$, $(CR_{10}R_{20})_nC(Z)NR_{16}R_{26}$, $(CR_{10}R_{20})_nC(Z)NR_{13}OR_9$, $(CR_{10}R_{20})_nNR_{10}C(Z)R_{11}$, $(CR_{10}R_{20})_nNR_{10}C(Z)NR_{16}R_{26}$, $(CR_{10}R_{20})_nN(OR_6)C(Z)NR_{16}R_{26}$, $(CR_{10}R_{20})_nN(OR_6)C(Z)R_{13}$, $(CR_{10}R_{20})_nC(=NOR_6)R_{13}$, $(CR_{10}R_{20})_nNR_{10}C(=NR_{19})NR_{16}R_{26}$, $(CR_{10}R_{20})_nOC(Z)NR_{16}R_{26}$, $(CR_{10}R_{20})_nNR_{10}C(Z)NR_{16}R_{26}$, $(CR_{10}R_{20})_nNR_{10}C(Z)OR_{10}$, 5-($R_{18}$)-1,2,4-oxadizaol-yl or 4-($R_{12}$)-5-$R_{18}R_{19}$)-,5-dihydro-1,2,4-oxadiazol-3-yl; wherein the aryl, arylalkyl, heteroaryl, heteroaryl alkyl, cyclcoalkyl, cycloalkyl alkyl, heterocyclic and heterocyclic alkyl groups may be optionally substituted;

More suitably $R_4$ is hydrogen, $NR_{16}R_{26}$, $NR_{10}C(Z)R_{11}$, $NR_{10}C(Z)NR_{16}R_{26}$, $NR_{10}C(=NR_{19})NR_6R_{26}$, or $NR_{10}C(Z)OR_{10}$. Preferably, $R_4$ is hydrogen 4or $NR_{16}R_{26}$. Preferably the $R_{16}$ and $R_{26}$ groups are independently hydrogen, or $C_{1-4}$ alkyl or $R_{16}$ and $R_{26}$ together with the nitrogen to which they are attached from a heterocyclic or heteroaryl ring of 5–7 members optionally containing an additional heteroatom selected from oxygen, sulfur or $NR_{22}$. The heterocyclic and heteroaryl ring may also be additionally substituted In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $C(Z)NR_8OR_9$, $NR_{10}C(Z)NR_8R_9$, or $OR_{25}$.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)mC_{1-10}$ alkyl, wherein m is 0, 1 or 2, such as methyl thio, methylsulfinyl or methyl sulfonyl; amino, mono & di-substituted amino, such as in the $NR_7R_{17}$ group; or where the $R_7R_{17}$ may together with the nitrogen to which they are attached cyclize to form a 5 to 7 membered ring which optionally includes an additional heteroatom selected from O/N/S; $C_{1-10}$ alkyl, cycloalkyl or cycloalkyl alkyl group, such as methyl, ethyl, propyl, isopropyl, t-butyl, etc. or cyclopoyl methyl; halosubstituted $C_{1-10}$ alkyl, such $CF_3$; an optionally substituted aryl, such as phenyl, or an optionally substituted arylalkql, such as benzyl or phenethyl, wherein these aryl moieties may also be substituted one to two times by halogen; hydroxy; hydroxy substituted alkyl; $C_{1-10}$ alkoxy; $S(O)_malkyl$; amino, mono and di-substituted amino, such as in the $NR_7R_{17}$ group; $C_{1-10}$ alkyl, or halo-substituted alkyl, such as $CF_3$.

In a preferred subgenus of compounds of formula (I), $R_1$ is 4-pyridyl, 2-alkyl-4-pyridyl, 2-$NR_{10}R_{20}$-4-pyridyl, 4-pyrimidinyl, 2-alkyl-4-pyrimidinyl, 2-$NR_{10}R_{20}$-4-pyrimidinyl, wherein one of $R_{10}R_{20}$ is hydrogen, or 4-quinolyl; more preferably $R_1$ is 2-amino-4-pyrimidinyl or 2 methylamino-4-pyrimidinyl; $R_2$ is an optionally substituted phenyl group. More preferably $R_2$ is phenyl or phenyl substituted by fluoro, chloro, $C_{1-4}$ alkoxy, $S(O)_mC_{1-4}$ alkyl, methanesulfonamido or acetamido; $R_3$ is phenyl or optionally substituted phenyl and $R_4$ is hydrogen or $NR_{16}R_{26}$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicynlc acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo;

"$C_{1-10}$ alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

The term "cycloalkyl" is used herein to mean cyclic radicals, preferably of 3 to 7 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy")—a 5–10 membered aromatic ring system in which one or more rings contain one or more heteroatoms selected from the group consisting of N, O or S, such as, but not limited to pyrrole, thiophene, quinoline, isoquinoline, pyridine, pyrimidine, oxazole, thiazole, thiadiazole, triazole, imidazole, or benzimidazole;

"heterocyclic" (on its own orin any combination, such as "heterocyclylalkyl")—a saturated or wholly or partially unsaturated 4–10 membered ring system in which one or more rings contain one or more heteroatoms selected from the group consisting of N, O, or S; such as, but not limited to, pyrolidine, piperidine, piperazine, morpholine, imidazolidine or pyrazolidine;

The term "aralkyl" or "heterorylalkyl" or "heterocyclicalkyl" is used herein to mean $C_{1-4}$ alkyl as defined above unless otherwise indicated "sulfinyl"—the oxide S(O) of the corresponding sulfide while the term "thio" refers to the sulfide.

The compounds of the present invention may contain one or more asymmetric carbon atoms and may exist in racemic and optically active forms. All of these compounds are included within the scope of the present invention.

Compounds of Formula (I) are pyrrazole derivatives which may be readily prepared using procedures well known to those of skill in the art and may be prepared by analogous methods to those indicated herein below.

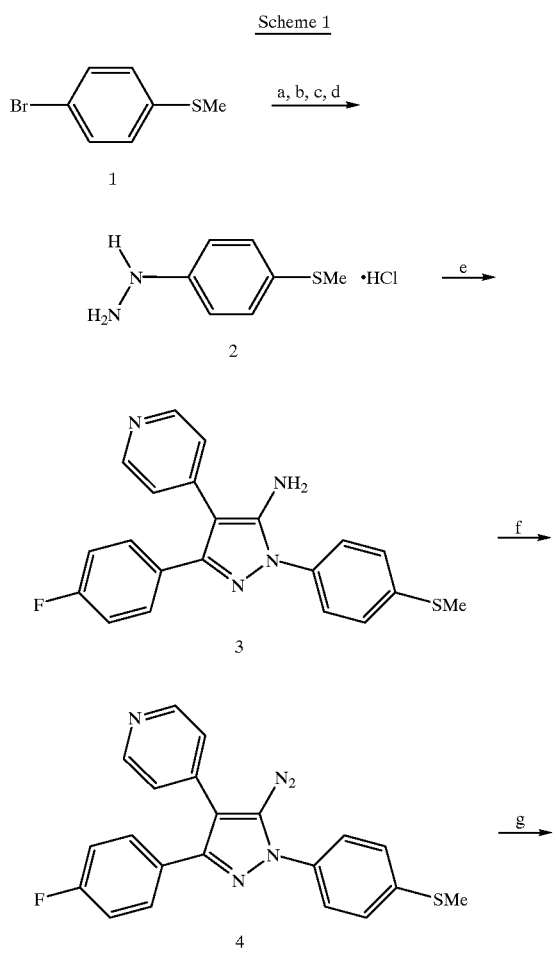

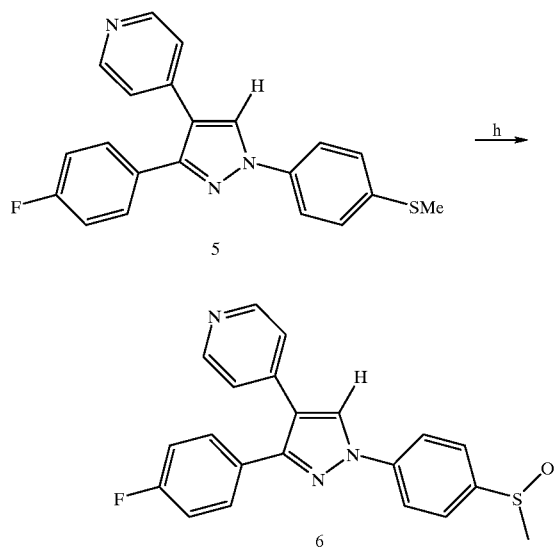

a) MgO; b) $(CH_3)_3CO_2CN$=$NCO_2C(CH_3)_3$ c) HOAc; d) HCl; e) 4-Py-CH(CN)CO-4-FPh; f) $NaNO_2$, HCl (aq); g) $Cu_2O$, $HOAC/H_2SO_4$, EtOH; h) $K_2S_2O_8$, HOAC, $H_2O$

While the illustration in Scheme I is for the preparation of a particular compound of Formula (I) (i.e., Scheme I, $R_1$=pyridyl, $R_2$=4-fluorophenyl, $R_3$=methylsulfinylphenyl and $R_4$ is amino or hydrogen), generalization of the synthesis to groups claimed as $R_1$, $R_2$, $R_3$ and $R_4$ herein can be achieved by starting with the appropriate propanenitrile, preparation of which are disclosed in EP 0 531 901 A2 whose disclosure is incorporated by reference herein. Treatment of the propanenitrile with the appropriate arylhydrazine affords 5-aminopyrazole, 3-Scheme 1 as outlined by Smith, P.A.S. et al., *J. Org. Chem.*, 1970, 35(7), 2215. Pyrazole 3-Scheme 1 can be converted to the corresponding sulphonamide, amide, urea, guanidine or urethane by using techniques well known to those of skill in the art by the appropriate acylating agents, such as sulfonyl chlorides, acid chlorides, isocyanates, dicyanamides and chlorofornates, respectively. 5-Aminopyrazole, 3-Scheme 1 can also be converted to the 5-diazopyrazole, 4-Scheme 1 by treatment with $NaNO_2$ and aqueous HCl. Following the procedure of Hodgson, H. H. et al., *J. Chem. So. London*, 1944, 8, treatment of 4-Scheme 1 with $Cu_2O$ and $HOAc)H_2SO_4$) affords pyrazole 5-Scheme I.

Alternatively any acylsubstituted malonate ester can be reacted with a substituted hydrazine derivative to afford a 3-hydroxypyrazole such as 1-Scheme 2. A 3-hydroxypyrazole can be either deoxygenated as shown in scheme II, or can also be converted to afford a suitable derivative. The ester functionality can be transformed into a methyl ketone such as 2-Scheme 2 which can be reacted with a variety of reagents like Bredrick's reagent or DMF dirnethylacetal, to yield an enamine such as 3-Scheme 2. Enamines (like 3-Scheme 2) react efficiently with guanidine derivatives (or substituted guanidine derivatives) to afford the corresponding 2-aminopyrimidine 4-Scheme 2.

Scheme II

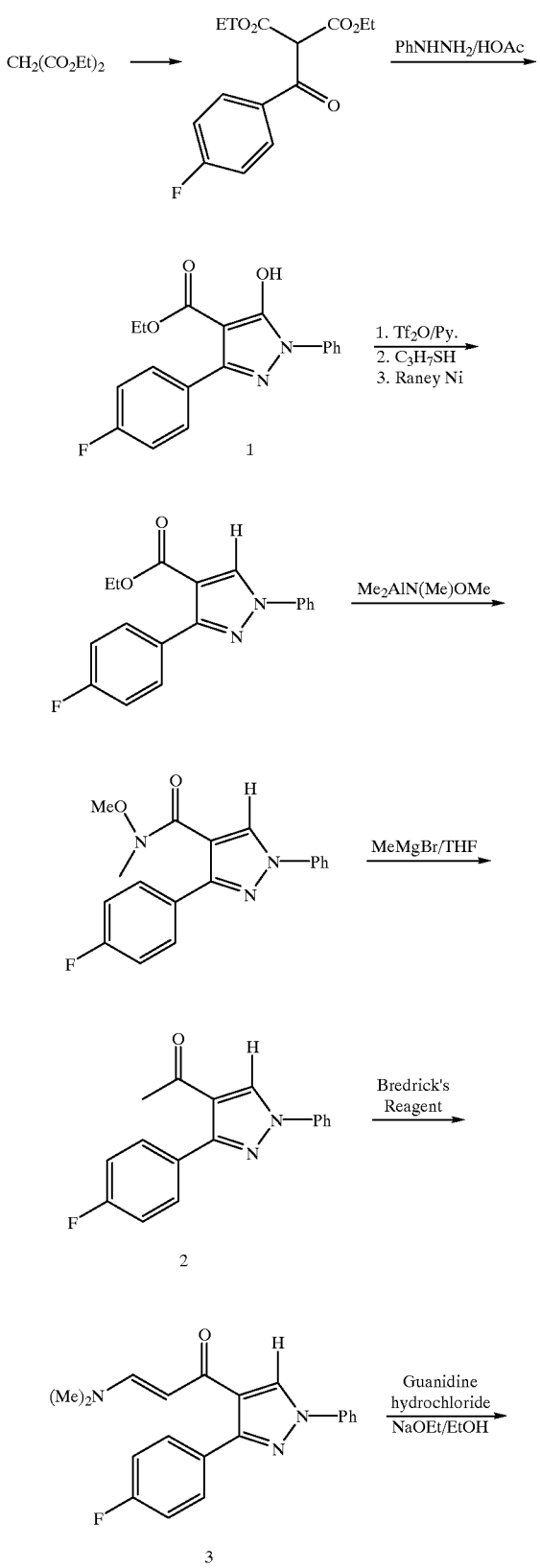

In addition to action with a thiol as illustrated in Scheme II, the triflate of compound 1-Scheme II can be reacted with both carbon and nitrogen nucleophiles to obtain compounds having $R_4$ not equal to hydrogen. For example, the triflate of 1-Scheme II can be displaced with either azide or cyanide to afford compound, which are themselves intermediates for the synthesis of compounds having respectively either a nitrogen (amines, amides, ureas) or carbon (ketones, esters, amides, alcohols) attachment to the pyrazole ring. Furthermore the triflate or the halo (chloro, bromo, or iodo) dcriyative, which may be prepared either from 1-Scheme II directly or from nucleophilic displacement of the triflate by the halo group, can be reacted under a variety of transition metal (Pd, Ni, etc.) catalyzed cross coupling conditions with a suitable organometallic based carbon nucleophiles (arylstannanes, boronic acids, organozincs) to afford $R_4$ as an aryl, heteroaryl, olefin, acetylene, ester, or alkyl substituent.

Alternatively, reaction of 3-Scheme II with S-methyl thiourea produces a 2-thiomethyl substituted pyrimidine (4-Scheme II with S-methyl in place of $NH_2$). This intermediate may be reacted under basic conditions with amine nucleophiles to produce analogs of 4-Scheme II (RHN in place of $NH_2$ wherein R is a suitable substituent group, such as $R_{13}$, $S(O)_2R$, etc.) or preferably oxidized to the sulfoxide or sulfone which then undergo more facile displacement with amine nucleophiles to afford the analogs of 4-Scheme II.

Suitable protecting groups for use in the present invention, are well known in the art and described in many references, for instance, Protecting Groups in Organic Synthesis, Greene T W, Wiley-Interscience, New York, 1981.

Pharmaceutically acid addition salts of compounds of formula (I) may be obtained in known manner, for example by treatment thereof with an appropriate amount of acid in the presence of a suitable solvent The invention will now be described by reference to the following examples which are merely illustrative and are not to be construed as a limitation of the scope of the present invention.

SYNTHETIC EXAMPLES

Example 1
3-(4-Fluorophenyl)-1-(4-methylsulfinylphenyl)-4-(4-pyridyl)-5H-pyrazole (a) 4-(Methylthio)phenylhydrazine hydrochloride—The title compound is prepared following the procedure of Demers, J. P. et al., *Tet. Lett.*, 1987, 28 (42), 4933.

(b) 3-(4-Fluorophenyl)-3-oxo-2-(pyridin-4-yl) propanenitrile—The title compound is prepared following the procedure of Oku, T. et al., EP 0 531 901 A2.

(c) 5-Amino-3-(4-fluorophenyl)-1-(methylthiophenyl)-4-(4-pyridyl)pyrazole—The title compound is prepared following the procedure of Smith, P. A. S. et al., *J. Org. Chem.*, 1970, 35 (7), 2215 except using 4-(methylthio) phenylhydrazine hydrochloide and 3-(4-fluorophenyl)-3-oxo-2-(pyridin-4-yl)propanenitrile.

(d) 5-Diazo-3-(4-fluorophenyl)-1-(methylthiophenyl)-4-(4-pyridyl)pyrazole—5-Amino-3-(4-fluorophenyl)-1-(methylthiophonyl)-4-(4-pyridyl)pyrazole is dissolved in a suitable volume of water containing 2.5–3 equivalents of HCl. The solution is cooled in ice and maintained at 5° C. while an aqueous soluton of $NaNO_2$ is added porionwise. The $NaNO_2$ is added until, after 3–4 min, the solution gives a positive result with a moist potassium iodide-starch paper test. The title compound is used without further purification.

(e) 3-(4-Fluorophenyl)-1-(metbylthiophenyl)-4-(4-pyridyl)-5H-pyrazole—The tide compound is prepared following the procedure of Hodgson, H. H. et al., *J. Chem. Soc. London*, 1944, 8, except using 5-diazo-3-(4fluorophenyl)-1-(methylthiophenyl)-4-(4-pyridyl)pyrazole.

(f) 3-(4-FIuorophenyl)-1-(4-methylsulfinylphenyl)-4-(4-pyridyl)-5H-pyrazole—A solution of 3-(4-fluorophenyl)-1-(methylthiophenyl)-4-(4-pyridyl)-5H-pyrazole in glacial acetic acid is added to an aqueous solution of $K_2S_2O_8$. The solution is stirred at rt for 18 h. The mixture is then poured into $H_2O$ and the pH is adjusted to neutral with conc. $NH_4OH$. The solid which is formed is collected to afford the title compound.

Example 2

4-(2-Amino-4-pyrimidinyl)-3-(4-fluorophenyl)-1-phenylpyrazole a) Diethyl-4-fluorobenzoy)maloante The title compound was prepared following the procedure of Lawesson, et al, *Acta Chem. Scand.*, 1959, 13 (8), 1717.

b) 5-Hydroxy-4-carboethoxy-3-(4-flurophenyl)-1-phenylpyrazole

Phenyl hydrazine (11.2 mL) was dissolved in 70% acetic acid/water (37 mL) and added dropwise to a solution of the compound of example 1(a) (6.38 g, 22.6 mmol) dissolved in glacial acetic acid (37 mL). The resulting mixture was allowed to stand at room temperature for 3 days before diluting with water and filtering. The resulting brown crystals were washed with water to afford the title compound (6.41 g, 87% yield). $^1$H NMR (400 MHz, $CDCl_3$): d 7.89 (d, 2H), 7.80 (q, 2H), 7.49 (t, 2H), 7.36 (t, 1H), 7.12 (t, 2H), 4.36 (q, 2H), 1.33 (t, 3H).

c) 4-Ethoxycarbonyl-3-(4-fluorophenyl)-1-phenylpyrazole

The compound of example 1(b) (0.30 g, 0.92 mmol) and 2,6-lutidine, (0.14 mL, 1.20 mmol) in $CH_2Cl_2$ were cooled to −30° C. Trifluoromethane sulfonic anhydride (0.17 mL, 1.01 mmol) was added and the mixture was allowed to stand at 0° C. for 24 h. The mixture was filtered and concentrated and the resulting oil was triturated with 5% EtOAc/Hexane until the remaining residue solidified. The organic washings were combined and concentrated The resulting oil was combined with 1-propanethiol (2 eq.) and $K_2CO_3$ (2 eq.) in DMF and stied at room temperature 24 h. The mixture was diluted with water and extracted with EtOAc. The organic phase was dried ($Na_2SO_4$) and concentrated. The resulting residue was purified by flash chromatography (silica gel, 0%–2% acetone/hexane). The isolated product was dissolved in ethanol and combined with activated Raney Nickel. The mixture was stirred 1 h. and was filtered through celite rinsing well with ethanol. Evaporation of the solvent afforded the title compound as a white solid (40% yield). $^1$H NMR (400 MHz, $CDCl_3$): d 8.50 (s, 1H), 7.90 (q, 2H), 7.78 (d, 2H), 7.51 (t, 2H), 7.39 (t, 1H), 4.32 (q, 2H), 1.35 (t, 3H).

d) N,O-dimethyl-3-(4-fluorophenyl)-1-phenypyrazole-4-hydroxamate

A suspension of N,O-dimethylhydroxylamine hydrochloride (0.39 g) in toluene (2 mL) was cooled to 0° C. Trimethylaluminum (2 mL, 2 M solution on toluene) was added slowly and the mixture was warmed to room temperature and stirred 1 h. This reagent (1.3 mL, 1.70 mmol) was added to the compound of example 1(c) (0.2 g, 0.68 mmol) dissolved in toluene (4 mL). After stirring at 80° C. for 2 h. the reaction was quenched by the addition of 3 N HCl and the product was extracted with EtOAc. The organic phase was dried ($Na_2SO_4$) and concentrated. The residue was suspended in 5% EtOAc/hexane and the resulting solid was filtered to afford the title compound as a white solid (0.15 g, 67% yield). $^1$H NMR (400 MHz, $CDCl_3$): d 8.35 (s, 1H), 7.78 (m, 4H), 750 (t, 2H), 7.34 (t, 1H), 7.11 (t, 2H), 3.60 (s, 3H), 3.31 (s, 3H).

e) 4-acetyl-3-(4-fluorophenyl)-1-phenylpyrazole

The compound of example 1(d) (0.11 g, 0.34 mmol) in dry TBF (7 mL) was cooled to −78° C. Methylmagnesium bromide (1.36 mmol, 3.0 M sln. in diethyl ether)was added and the solution was warmed to room temperature. The reaction was quenched with saturated, aqueous $NH_4Cl$. The product was extracted with EtOAc. The organic phase was dried ($Na_2SO_4$) and concentrated to yield the title compound (0.09 g, 97% yield). $^1$H NMR (400 MHz, $CDCl_3$): d 8.74 (s, 1H), 7.70 (m, 4H), 7.51 (t, 2H), 7.40 (t, 1H), 7.15 (t, 2H), 2.47 (s, 3H).

f) 4[(3-N,N-dimethyl)-prop-2-ene-1-one]-3-(4-fuorophenyl)-1-phenylpyrazole

Added to the compound of example 1(e) (0.09 g, 0.33 mmol) in DMF (5 mL) was tert-butylbis(dimethylamino) methane (0.20 mL, 0.99 mmol). The mixture was stirred at 110° C. for 4 h. and then concentrated. The resulting residue was purified by flashed chromatography eluting with 2% $MeOH/CH_2Cl_2$ to afford the title compound (0.11 g, 99% yield). $^1$H NMR (400 MHz, $CDCl_3$): d 8.35 (s, 1H), 7.78 (m, 4H), 7.65 (d, 1H), 7.45 (t, 2H), 7.29 (t, 1H), 7.08 (t, 2H), 5.20 (d, 1H), 3.03 (s, 3H), 2.66 (s, 3H).

g) 4-(2-amino-4-pyrimidinyl)-3-(4-fluorophenyl)-1-phenylpyrazole

Sodium (0.0075 g, 0.33 mmol) was dissolved in ethanol (1 mL). Guanidine hydrocloride (0.03 g, 0.33 mmol) was added and the mixture was stirred 10 min. The compound of example 1(f) (0.11 g, 0.33 mmol) was dissolved in ethanol (5 mL) and added to the mixture and refluxed for 18 h. The resulting mixture was cooled and concentrated. The residue was triturated with $CH_2Cl_2$ and filtered The organic extract was concentrated. The product was crystal from ethanol to afford the title compound (0.05 g, 52% yield). mp 170–171° C. $^1$H NMR (400 MHz, $CDCl_3$): d 8.51 (s, 1H), 8.16 (d, 1H), 7.80 (d, 2H), 7.62 (q, 2H), 7.50 (t, 2H), 7.36 (t, 1H), 7.14 (t, 1H), 6.49 (d, 1H), 5.01(s, 2H).

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytocine production by such mammal's cell, such as, but not limited to monocytes and/or macrophages.

Compounds of formula (I) are capable of inhibiting proinflammatory cytokines, such as IL-1, IL-6, IL-8 and TNF and are therefore of use in therapy. IL-1, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of formula (I) or a pharmaceutically acceptable salt thereof.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic βcells and Alzheimer's disease.

In a further aspect, this invention relates to a method of inhibiting the production of TNF in a mammal in need thereof which comprises administering to said mammal an effective amount of a compound of formula (I) or a pharmaceutically acceptable salt thereof.

Excessive or unregulated TNF production has been implicated in mediating or exacerbating a number of diseases including rheumatoid arthritis, rheumatoid spondylitis, osteoartritis, gouty arthritis and other arhritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

Compounds of formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Another aspect of the present invention relates to a method of inhibiting the production of IL-8 (Interleulin-8, NAP) in a mammal in need thereof which comprises administering to said mammal an effective amount of a compound of formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal repcrfision injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL-8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of EL-1, IL-8 or TNF mRNA above basal levels in cells or tissues in which IL-1, IL-8 or TNF, respectively, is produced.

The discovery that the compounds of formula (I) are inhibitors of cytokines, specifically IL-1, IL-8 and TNF is based upon the effects of the compounds of formula (I) on the production of the IL-1, IL-8 and TNF in in vitro assays which are described herein.

As used herein, the term "inhibiting the production of IL-1 (IL-8 or TNF)" refers to:

a) a decrease of excessive in vivo levels of the cytokine (IL-1, IL-8 or TNF) in a human to normal or subnormal levels by inhibition of the in vivo release of the cytokine by all cells, including but not limited to monocytes or macrophages;

b) a down regulation, at the genomic level, of excessive in vivo levels of the cytokine (IL-1, IL-8 or TNF) in a human to normal or sub-normal levels;

c) a down regulation, by inhibition of the direct synthesis of the cytokine (IL-1, IL-8 or TNF) as a postranslational event; or d) a down regulation, at the translational level, of excessive in vivo levels of the cytokine (IL-1, IL-8 or TNF) in a human to normal or subnormal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monolines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-β).

As used herein, the term "cytokine interfering" or "cytokine suppressive amount" refers to an effective amount of a compound of formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterelly or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lodon may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaccous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

The invention will now be described by reference to the following examples which are merely illustrative and are not to be construed as a limitation of the scope of the present invention.

BIOLOGICAL EXAMPLES

The cytokine-inhibiting effects of compounds of the present invention are determined by the following in vitro assays:

Interleukin 1 (IL-1)

Human peripheral blood monocytes are isolated and purified from either fresh blood preparations from volunteer donors, or from blood bank buffy coats, according to the procedure of Colotta et al, *J Immunol*, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., *J. Immunol. Methods*, 84, 85, (1985) (based on ability of IL-1 to stimulate a Interleukin 2 producing cell line (EL-4) to secrete IL-2, in concert with A23187 ionophore) or the method of Lee et a., *J. ImmunoTherapy*, 6 (1), 1–12 (1990) (ELISA assay).

Tumor Necrosis Factor (TNF)

Human peripheral blood monocytes are isolated and purified from either blood bank buffy coats or plateletphemsis residues, according to the procedure of Colotta, R et al., *J Immunol*, 132(2), 936 (1984). The monocytes are plated at a density of $1 \times 10^6$ cells/ml medium/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds were solubilized in dimethyl sulfoxide/ethanol, such that the final solvent concentration in the culture median is 0.5% dimethyl sulfoxide/0.5% ethanol). Bacterial lipopoly-sacchuride (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., *J Immunol*, 1991, 147, 4307.

Interleukin 8 (IL-8)

Primary human umbilical cord endothelial cells (HUVEC) (Cell Systems, Kirland, Wash.) are maintained in culture medium supplemented with 15% fetal bovine serum and 1% CS-HBGF consisting of a FGF and heparin. The cells are then diluted 20fold before being plated (250 μl) into gelating coated 96-well plates. Prior to use, culture medium is replaced with fresh medium (200 μl). Buffer or test compound (25 μl, at concentrations between 1 and 10 μM)

is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$'s where appropriate are generated by non-linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible CSAID binding assay was developed using soluble cystosolic fraction from THP.1 cells and a radiolabeled compound. For instance, a suitable radiolabeled compound of the CSAID class is 4-(Fluorophenyl)-2-(4-hydroxyphenyl-3,5-$t_2$)-5-(4-pyridyl)imidazole. In brief, the THP.1 cytosol was routinely prepared from cell lysate obtained by nitrogen cavitation followed by a 10 K×g low speed and a 100 K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 mMb—mercaptoethanol, $NaN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present. Compounds of Formula (I) at various doses are added to the binding assay to achieve inhibition of binding of the radiolabel. $IC_{50}$s as well as Ki values are determined by regression analysis and scatchard plot analysis respectively. There is generally excellent correlation between the $IC_{50}$ of compounds tested in both the binding assay and the bioassay and can be used interchangeably in many cases.

Compounds of Formula (I), as illustrated by Example 2, herein was shown to have activity in the CSBP assay.

Patent Application U.S. Ser. No. 081123,175 Lee et al., filed Sep. 17, 1993 and Ser. No. 08/250,975 published as WO 95/07922 on Mar. 23, 1995 now U.S. Pat. No. 5,783,664 whose disclosures are incorporated by reference herein in its entirety describes the above noted method for screening drugs to identify compounds which interact with and bind to the CSBP. However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the screening protocol. Regardless of the form of the binding protein, a plurality of compounds are contacted with the binding protein under conditions sufficient to form a compound/binding protein complex and compound capable of forming, enhancing or interfering with said complexes are detected.

More specifically, the CSAID Binding Assay is performed as follows:

Materials

Incubation buffer: 20 mM Tris, 1 mM $MgCl_2$, 20 mM Hepes, 0.02% $NaN_3$, store at 4° C.

Elution buffer: 20 mM Tris, 50 mM 2-mercaptoethanol, $NaN_3$, store at 4° C. G-10 Sephadex: add 100 g Sephadex G-10 (Pharmacia, Uppsala, Sweden) to 400 mL dd $H_2O$ and allow to swell at room temperature for 2 hours. Decant fines and wash 3 times. Add $NaN_3$ and qs with dd $H_2O$ to 500 mLs and store at 4° C.

Assemble Columns: Straw column, filter frit and tip (Kontes, SP 420160-000, 420162-002). Lowsorb tubes (Nunc) used in binding reaction. THP.1 cytosol spun at 15000 rpm for 5 min to clarify. THP.1 cytosol prepared by hypnotic treatment of cells and lysis by decompression in nitrogen. Nuclei and membrane fragments removed by differential centriflgation (10,000 g for 1 hour and 100,000 g for 1 hour).

Compounds: Non-radioactive Compound I with corresponding EtOH control (dilutions made in incubation buffer) and $^3$H-Compound I (dilutions in incubation buffer)

Method

A. Column Preparation
 1. Begin 30 min before anticipated elution of reaction mixture.
 2. Add 3 mL of G-10 slurry to column for bed vol of 1.5 ml.
 3. Rinse with 7 mL elution buffer (fill to top of column).
 4. Cut columns down to size.

B. Sample Incubation
 1. 15 min incubation at 4° C.
 2. Binding reaction mixture; 100 µL cytosol, 10 µL cold Compound I or EtOH control, 10 µL $^3$H-Compound I (molar concentration depends on nature of study).
 3. "Free" control=100 µL incubation buffer in lieu of cytosol preparation.

C Sample Elution
 1. Elute at 4° C.
 2. Add total fraction volume to G-10 column.
 3. Add 400 µL elution buffer to column and discard eluate.
 4. Add 500 µL elution buffer to column, collecting eluted volume in 20 ml scintillation vial.
 5. Add 15 mL Ready Safe scintillation fluid.
 6. Vortex and count in liquid scintillation counter for 5 minutes. Include a "total input counts control" (10 µL of labeled ligand).

D. Data Analysis
 1. Plot DPMS as ouptut in graphic form and analyze by regression analysis and "Lundon ligand binding" software for the determination of IC 50 and Kd/Ki respectively.
 2. Rank order the $IC_{50}$s of the tested compounds in the CSAID bioassay and compare to that generated by the CSAID binding assay and establish a correlation curve.

The binding assay was further validated by the following criteria: THP.1 cytosol demonstrated saturable and specific binding of the radiolabeled compound.

Preparation of 4-(Fluorophenyl)-2-(4-hydroxyphenyl-3,5-$t_2$)-5-(4-pyridyl)imidazole, (Comnpound I). A 2.9 mg (0.0059 mmol) portion of 2-(3,5-Dibromo-4-hydroxyphenyl)-4-(4-fluorophenyl)-5-(4-pyridyl)imidazole, Compound I(p), was dissolved in 0.95 mL of dry DMF and 0.05 mL of triethylamine in a 2.4 mL round bottom flask equipped with a small magnetic stirring bar. A 1.7 mg portion of 5% Pd/C (Engelhard lot 28845) was added, and the flask was attached to the stainless steel tritium manifold.

The mixture was degassed through four freeze-pump-thaw cycles, then tritium gas (5.3 Ci, 0.091 mmol) was introduced. The reaction mixture was allowed to warm to room temperature and was stirred vigorously for 20 h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were re moved by static vacuum transfer. A 1.5 mL portion of methanol was added to the residue, then removed by static vacuum transfer. The latter process was repeated. Finally, the residue was suspended in 1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Partisil 5 ODS-3, 4.6 mm I.D.×25 cm, 1 ml/min of 70:30:01 water/acetonitrile/trifluoroacetic acid, Radiomatic Flo-One Beta radio detector with 3 mL/min of Ecoscint-H cocktail through a 0.75 mL cell) showed the presence of Compound I($R_t$=60 min. ca. 37% of total radioactivity), and a discrete intermediate presumed to be the monobromo derivative Compound Ia $R_t$=11.8 min, ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia are collected separately.

| HPLC Method | |
| --- | --- |
| Column | Altex Ultrasphere 10 mm I.D. × 25 cm |
| Mobile Phase | 70:30:0.1 water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I |
| | 24 min Compound Ia |

The pooled Compound I fractions totaled 32 mL in volume and the radioactive concentration was 1.52 mCi/mL (total 48.6 mCi). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness in vacua at <35° C., then redissolved in 0.5 mL of mobile phase. The whole volume was injected into the HPLC system described above, and the appropriate peak was collected. Evaporation of the collected eluate in vacua at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in CD$_3$OD.

Analysis of 4-(4-Fluorophenyl)-2-(4-hydroxyphenyl-3,5-t$_2$)-5-(4-pyridyl)imidazole, Compound I.

| Radiochemical Purity by HPLC | |
| --- | --- |
| Method | |
| Column | Ultrasphere Octyl, 5 mm, 4.6 mm I.D. × 25 cm, Beckman |
| Mobile Phase | 350:150:0.5 (v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count (Tru-Lab Supply Co.) |
| Flow rate | 5.0 mL/min |
| Cell volume | 0.75 mL |
| Retention time | 7.7 min |
| Result | 98.7 |

| Radioactive Concentration by Scintillation Counting | |
| --- | --- |
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |

| Specific Activity by Mass Spectrometry | |
| --- | --- |
| Method | CI-MS, NH$_3$ reagent gas |
| Result | 20.0 Ci/mmol |
| | $^3$H Distribution: |
| | Unlabeled 44% |
| | Single Label 43% |
| | Double Label 13% |

| $^3$H NMR$^9$ | |
| --- | --- |
| Method | |
| Instrument | Brunker AM 400 |
| Experiment | Proton decoupled $^3$H NMR |
| | Proton non-decoupled $^3$H NMR |
| | Proton non-decoupled $^3$H NMR |
| Peak Referencing Solvent | Solvent Peak of methanol 63.3 |
| | Methanol-d$_4$ |
| Result | Tritium is incorporated exclusively on the carbon atoms ortho to aromatic hydroxyl group |

| Analytical Summary | |
| --- | --- |
| Assay | Result |
| Radiochemical purity determined by HPLC | 98.7% |
| Radioactivity concentration determined by scintillation counting | 2.44 mCi/mL |
| Specific activity determined by mass spectrometry | 20.0 Ci/mmol |
| $^3$H NMR | agrees with the proposed structure |

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:
1. A compound of the formula:

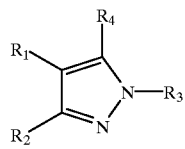

(I)

wherein
one of $R_1$ and $R_2$ is a 4-pyridyl ring, which ring is optionally substituted with one or two substituents each of which is independently selected from $C_{1-4}$ alykl, halo, $C_{1-4}$ alkoxy, $C_{1-4}$ alkylthio, $CH_2OR_8$, $NH_2$, mono- or di-$C_{1-6}$-alkylamino or N-heterocyclyl ring selected from pyrrolidine, piperidine, piperazine, morpholine, imidazolidine, and pyrazolidine;

the other of $R_1$ and $R_2$ is selected from an optionally substituted phenyl ring, or naphthyl ring, which ring is substituted by one or two substituents, each of which is independently selected, and which, for a 4-phenyl, 4-naphth-1-yl or 5-naphth-2-yl substituent, is halo, nitro, cyano, $C(Z)NR_7R_{17}$, $C(Z)OR_{23}$, $(CR_{10}R_{20})_nCOR_{36}$, $SR_5$, $S(O)R_5$, $OR_{36}$, halo-substituted $C_{1-4}$ alkyl, $C_{1-4}$ alkyl, $ZC(Z)R_{36}$, $NR_{10}C(Z)R_{23}$, or $(CR_{10}R_{20})_nNR_{10}R_{20}$ and which, for other positions of substitution, is halo, $(CR_{10}R_{20})_n$nitro, $(CR_{10}R_{20})_n$cyano, $(CR_{10}R_{20})_nC(Z)NR_{16}R_{26}$, $(CR_{10}R_{20})_nC(Z)OR_{18}$, $(CR_{10}R_{20})_nCOR_{25}$, $(CR_{10}R_{20})_n$—$S(O)_mR_8$, $(CR_{10}R_{20})_nOH$, $(CR_{10}R_{20})_nOR_{25}$, halo-substituted-$C_{1-4}$ alkyl, $C_{1-4}$ alkyl, $(CR_{10}R_{20})_nNR_{10}C(Z)R_{25}$, $(CR_{10}R_{20})_nNHS(O)_mR_6$, $(CR_{10}R_{20})_nNHS(O)_mNR_7R_{17}$, $(CR_{10}R_{20})_nNR_6S(O)_mR_6$, $(CR_{10}R_{20})_nNR_6S(O)_m'NR_7R_{17}$; $(CR_{10}R_{20})_nZC(Z)R_{18}$ or $(CR_{10}R_{20})_nNR_7R_{17}$;

n is 0 or an integer of 1 or 2;
m is 0 or an integer of 1 or 2;
m' is an integer of 1 or 2;
$R_3$ is Q-$(Y_1)_t$;
Q is a pyridyl group;
t is an integer having a value of 1 to 3;
$R_4$ is hydrogen, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$ alykl, aryl, aryl$C_{1-10}$ alkyl, $(CR_{10}R_{20})_nOR_{12}$, $(CR_{10}R_{20})_nOR_{13}$, $(CR_{10}R_{20})_nS(O)_mR_{18}$, $(CR_{10}R_{20})_nNHS(O)_2R_{18}$, $(CR_{10}R_{20})_nNR_{16}R_{26}$, $(CR_{10}R_{20})_nNO_2$, $(CR_{10}R_{20})_nCN$, $(CR_{10}R_{20})_nSO_2R_{18}$, $(CR_{10}R_{20})_nS(O)_mNR_{16}R_{26}$, $(CR_{10}R_{20})_nC(Z)R_{13}$, $(CR_{10}R_{20})_nOC(Z)R_{13}$, $(CR_{10}R_{20})_nC(Z)OR_{13}$, $(CR_{10}R_{20})_nC(Z)NR_{16}R_{26}$, $(CR_{10}R_{20})_nC(Z)NR_{13}OR_9$, $(CR_{10}R_{20})_nNR_{10}C(Z)R_{11}$, $(CR_{10}R_{20})_nNR_{10}C(Z)NR_{16}R_{26}$, $(CR_{10}R_{20})_nN(OR_6)C(Z)NR_{16}R_{26}$, $(CR_{10}R_{20})_nN(OR_6)C(Z)R_{13}$, $(CR_{10}R_{20})_nC(=NOR_6)R_{13}$, $(CR_{10}R_{20})_nNR_{10}C(=NR_{19})NR_{16}R_{26}$, $(CR_{10}R_{20})_nOC(Z)NR_{16}R_{26}$, $(CR_{10}R_{20})_nNR_{10}C(Z)NR_{16}R_{26}$, $(CR_{10}R_{20})_nNR_{10}C(Z)OR_{10}$, wherein the aryl, arylalkyl, cyclcoalkyl, cycloalkyl alkyl groups may be optionally substituted;

$R_6$ is $C_{1-10}$ alkyl, $C_{3-7}$ cycloalkyl, aryl, aryl$C_{1-10}$alkyl;
$R_5$ is hydrogen, $C_{1-4}$ alkyl, $C_{2-4}$ alkenyl, $C_{2-4}$ alkynyl or $NR_7R_{17}$, excluding the moieties—$SR_5$ being —$SNR_7R_{17}$ and —$SOR_5$ being —$SOH$;

$R_{16}$ and $R_{26}$ are independently hydrogen, or $C_{1-4}$alkyl or $R_{16}$ and $R_{26}$ together with the nitrogen to which they are attached form a heterocyclic selected from pyrrolidine, piperidine, piperazine, morpholine, imidazolidine, and pyrazolidine;

$Y_1$ is independently selected from hydrogen, $C_{1-5}$ alkyl, halo-substituted $C_{1-5}$ alkyl, halogen, or —$(CR_{10}R_{20})_nY_2$;

$Y_2$ is hydrogen, halogen, $OR_8$, $NO_2$, $S(O)_m'R_{11}$, $SR_8$, $S(O)_m'OR_8$, $S(O)_mNR_8R_9$, $NR_8R_9$, $O(CR_{10}R_{20})_n'NR_8R_9$, $C(O)R_8$, $CO_2R_8$, $CO_2(CR_{10}R_{20})_m''CONR_8R_9$, $ZC(O)R_8$, $CN$, $C(Z)NR_8R_9$, $NR_{10}C(Z)R_8$, $C(Z)NR_8OR_9$, $NR_{10}C(Z)NR_8R_9$, $NR_{10}S(O)_m'R_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR_{13})ZR_{11}$, $OC(Z)NR_8R_9$, $NR_{10}S(O)_mCF_3$, $NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl;

n' is 0 or an integer having a value of 1 to 10;
m" is an integer having a value of 1 to 10;
$R_7$ and $R_{17}$ is each independently selected from hydrogen or $C_{1-4}$ alkyl or $R_7$ and $R_{17}$ together with the nitrogen to which they are attached form a heterocyclic ring selected from pyrrolidine, piperidine, piperazine, morpholine, imidazolidine, and pyrazolidine;

$R_8$ is hydrogen, $C_{1-10}$ alkyl, $C_{3-7}$ cycloalkyl, aryl, aryl$C_{1-10}$alkyl;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, or $R_8$ and $R_9$ may together with the nitrogen to which they are attached form a heterocyclic selected from pyrrolidine, piperidine, piperazine, morpholine, imidazolidine, and pyrazolidine;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$, aryl, aryl $C_{1-10}$alkyl;

$R_{12}$ is hydrogen, —$C(Z)R_{13}$, optionally substituted $C_{1-4}$ alkyl, optionally substituted aryl, optionally substituted aryl-$C_{1-4}$ alkyl, or $S(O)_2R_{18}$;

$R_{13}$ is hydrogen, $C_{1-10}$alkyl, $C_{3-7}$ cycloalkyl, aryl, aryl$C_{1-10}$alkyl;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{18}$ is $C_{1-10}$ alkyl, $C_{3-7}$ cycloalkyl, aryl, aryl$C_{1-10}$alkyl;

$R_{19}$ is hydrogen, cyano, $C_{1-4}$ alkyl, $C_{3-7}$ cycloalkyl or aryl;

$R_{21}$ is hydrogen, a pharmaceutically acceptable cation, $C_{1-10}$ alkyl, $C_{3-7}$ cycloalkyl, aryl, aryl $C_{1-4}$ alkyl, aroyl, or $C_{1-10}$ alkanoyl;

$R_{22}$ is $R_{10}$ or $C(Z)$-$C_{1-4}$ alkyl;

$R_{23}$ is $C_{1-4}$ alkyl, halo-substituted-$C_{1-4}$ alkyl, or $C_{3-7}$ cycloalkyl;

$R_{25}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$alkyl, $(CR_{10}R_{20})_nOR_8$, $(CR_{10}R_{20})_nS(O)_mR_{18}$, $(CR_{10}R_{20})_nNHS(O)_2R_{18}$, $(CR_{10}R_{20})_nNR_7R_{17}$; wherein the aryl, or arylalkyl may be optionally substituted;

$R_{36}$ is hydrogen or $R_{23}$;

Z is oxygen;

Aryl is phenyl or naphthyl;

or a pharmaceutically acceptable salt thereof.

2. The compound according to claim 1 wherein $R_1$ is a substituted 4-pyridyl.

3. The compound according to claim 2 wherein the optional substituent is $C_{1-4}$ alkyl, amino, or mono substituted $C_{1-6}$ alkyl amino.

4. The compound according to claim 1 wherein $R_2$ is an optionally substituted phenyl.

5. The compound according to claim 4 wherein one or more optional substituents are in dependently selected from halogen or methoxy.

6. The compound according to claim 1 wherein $R_4$ is hydrogen, $NR_{16}R_{26}$, $NR_{10}C(Z)R_{11}$, $NR_{10}C(Z)NR_{16}R_{26}$, $NR_{(10)}C(=NR_{19})NR_{16}R_{26}$ or $NR_{10}C(Z)OR_{10}$.

7. The compound according to claim 6 wherein $R_{16}$ and $R_{26}$ are hydrogen, optionally substituted $C_{1-4}$ alykl, or $R_{16}$ and $R_{26}$ together with the nitrogen to which they are attached form a heterocyclic ring selected from pyrrolidine, piperidine, piperazine, morpholine, imidazolidine, and pyrazolidine.

8. The compound according to claim 5 wherein the halogen is 4-fluoro.

9. A pharmaceutical composition comprising a pharmaceutically acceptable carrier or diluent and a compound according to claim 1.

10. A method of treating arthritis, or other arthritic condition, in a mammal in need thereof which method comprises administering to said mammal an effective amount of a compound according to claim 1.

* * * * *